United States Patent [19]

Tabibi et al.

[11] Patent Number: 5,164,191
[45] Date of Patent: Nov. 17, 1992

[54] LIPID VESICLES HAVING AN ALKYD AS A WALL-FORMING MATERIAL

[75] Inventors: S. Esmail Tabibi, Chelmsford, Mass.; An-Cheng Chang, Nashua, N.H.; Rajiv Mathur, Nashua, N.H.; Donald F. H. Wallach, Hollis, N.H.

[73] Assignee: Micro Vesicular Systems, Inc., Nashua, N.H.

[21] Appl. No.: 654,327

[22] Filed: Feb. 12, 1991

[51] Int. Cl.$^5$ .............................................. A61K 37/22
[52] U.S. Cl. ...................................... 424/450; 424/420; 424/501; 428/402.2; 554/164; 554/173; 554/227
[58] Field of Search ............... 424/450, 420, 418, 501; 428/402.2; 264/4.1, 4.3, 4.6; 260/404.8; 554/164, 173, 227

[56] References Cited

U.S. PATENT DOCUMENTS

| | | | |
|---|---|---|---|
| 3,069,370 | 12/1962 | Jensen et al. | 260/23 |
| 3,345,313 | 10/1967 | Ruhe et al. | 260/404.8 X |
| 3,372,201 | 5/1968 | Leary et al. | 260/615 |
| 3,442,835 | 5/1969 | Curtice | 554/164 |
| 3,480,575 | 11/1969 | Coats | 260/404.8 |
| 3,575,882 | 4/1971 | Vandegaer et al. | 424/419 X |
| 3,586,653 | 6/1971 | Fritz | 260/404.8 |
| 3,943,063 | 3/1976 | Morishita et al. | 424/419 X |
| 4,241,046 | 12/1980 | Papahadjopoulos | 424/19 |
| 4,247,411 | 1/1981 | Vanlerberghe et al. | 252/316 |
| 4,271,344 | 8/1980 | Vanlerberghe et al. | 424/60 |
| 4,346,044 | 8/1982 | Dhein et al. | 260/404.8 |
| 4,356,167 | 10/1982 | Kelly | 424/38 |
| 4,377,567 | 3/1983 | Geno | 424/1 |
| 4,413,116 | 11/1983 | Reuter et al. | 260/404.8 X |
| 4,544,545 | 10/1985 | Ryan et al. | 424/1.1 |
| 4,551,288 | 11/1985 | Kelly | 264/4.6 |
| 4,666,711 | 5/1987 | Vanlerberghe et al. | 424/70 |
| 4,670,246 | 6/1987 | Dahl et al. | 424/419 |
| 4,744,989 | 5/1988 | Payne et al. | 424/490 |
| 4,762,915 | 8/1988 | Kung et al. | 530/405 |
| 4,772,471 | 9/1988 | Vanlerberghe et al. | 424/450 |
| 4,789,633 | 12/1988 | Huang et al. | 435/240 |
| 4,855,090 | 8/1989 | Wallach | 264/4.1 |
| 4,897,308 | 1/1990 | Vanlerberghe et al. | 428/402 |
| 4,917,951 | 4/1990 | Wallach | 428/402 |
| 5,021,200 | 9/1961 | Vanlerberghe et al. | 264/4.3 |
| 5,032,457 | 7/1991 | Wallach | 428/402 |

FOREIGN PATENT DOCUMENTS

| | | |
|---|---|---|
| 0402615 | 4/1970 | Austria . |
| 8706499 | 5/1987 | PCT Int'l Appl. . |
| 1165373 | 9/1969 | United Kingdom . |
| 1539625 | 1/1979 | United Kingdom . |
| 2078543 | 1/1982 | United Kingdom . |
| 2147263 | 5/1985 | United Kingdom . |
| 2166107 | 4/1986 | United Kingdom . |

OTHER PUBLICATIONS

Mattson J. Lipid Res. 5 #3, p. 374, 1964.
McCuthcheon, "Detergents and Emulsifiers", No. American Edition (1973).
Szoha et al., Proc. Nat'l. Acad Sci. USA 75:4194-4198 (1978).
Baillie et al., J. Pharm. Pharmacol. 37:863-868 (1985).
Baille et al., J. Pharm. Pharmacol 38:502-505 (1986).
Ribier et al, Colloids and Surfaces 10:155-161 (1984).

*Primary Examiner*—Thurman K. Page
*Assistant Examiner*—G. S. Kishore

[57] ABSTRACT

The present invention features a method of making lipid vesicles and the lipid vesicles themselves made from monomeric and dimeric alkyds. These alkyds are esters made as a condensation product of a first reactant having at least one free hydroxyl group and a $C_{12}$–$C_{20}$ fatty acids chain and a second reactant which is an aromatic acid chloride or anhydride. Preferred first reactants are esters of polyols and $C_{12}$–$C_{20}$ fatty acids, ethers of polyols and $C_{12}$–$C_{20}$ fatty acids, and $C_{12}$–$C_{20}$ fatty alcohols.

2 Claims, No Drawings

LIPID VESICLES HAVING AN ALKYD AS A WALL-FORMING MATERIAL

BACKGROUND OF THE INVENTION

The present invention relates to the production of lipid vesicles using an anionic material as the primary lipid in the vesicle walls. More particularly, a neutralized ester in the form of a monomeric or dimeric alkyd is used to form lipid vesicles.

A substantial number of different materials are described in the literature as being useful to form lipid vesicles. The first lipid vesicles, called liposomes, used phospholipid materials such as phosphatidyl choline as the primary structural lipid. Most of these phospholipids are dual chain zwitterions. Several cationic materials such as quaternary ammonium compounds and certain betaines have also been tried. More recently, non-ionic materials such polyoxyethylene ethers and esters have been used successfully to form lipid vesicles by both L'Oreal and Micro Vesicular Systems. While these non-ionic materials have certain advantages compared with phospholipids and quaternary ammonium compounds in terms of cost and the ability to be used in very rapid vesicle forming processes, it is occasionally Preferred to use a charged vesicle former.

There are few reports of anionic materials being successful as lipid vesicle forming materials. Micro Vesicular Systems has used sarcosinates to form vesicles; however, these materials will only form vesicles at non-neutral pH. In addition, there are reports of the use of certain fatty acids to form vesicles, e.g., the so-called "ufasomes," but these vesicles do not appear to be particularly stable. In addition, the processes described for making of ufasomes are very slow.

The most common industrial use of anionic materials having large fatty acid chains are in the formation of polyesters such as nylon, dacron, and the alkyds used in the paint industry. All of these polyesters have a highly polymerized structure, either as linear polymers, e.g., nylon fibers, or as a highly cross-linked structure, e.g., the laquers or alkyd resins used in the paint industry. Polymerization proceeds rapidly with these materials. Because the polymers have been so important industrially, there has been little work with the monomeric forms of these materials.

The alkyds used in the paint industry are normally made in a two step, three component, reaction. First, a fatty acid, preferably a $C_{16}-C_{18}$ fatty acid, is reacted with a polyol such as glycerol or pentaerythitol to form a monoglycercide. This monoglyceride is then reacted with a dianhydride such as phthalic, isophthalic, or trimellitic anhydride under conditions whereby polymerization takes place. These highly polymerized molecules, called alkyds, are used to act as the sealer in oil based paints. These alkyds are soluble in certain oils and organic solvents (but not in water) so they are used only in the oil based paints. However, these alkyds are not used in the monomeric or dimeric form since the polymerized form, which is highly cross-linked, is necessary for a long lasting finish. In fact, until the present invention, these alkyds have not been considered for use as vesicle formers.

Accordingly, an object of the invention is to provide lipid vesicles, and a method of making lipid vesicles, using anionic esters such as alkyds.

Another object of the invention is to provide anionic vesicles without adding a separate charge-producing agent.

A further object of the invention is to provide pH sensitive vesicles using materials which will form vesicles at neutral or higher pH while disintegrating at acid pH.

These and other objects and features of the invention will be apparent from the following description.

SUMMARY OF THE INVENTION

The present invention features lipid vesicles having a monomeric or dimeric alkyd as the primary wall-forming material. These wall-forming materials are anionic so a separate charge-producing agent is not necessary to prevent vesicle aggregation. The invention further features a method of making lipid vesicles using these wall-forming materials.

It has been discovered that certain monomeric or dimeric fatty acid esters having aromatic head groups such as alkyds can be used as the primary wall-forming lipid material for lipid vesicles. The alkyds are condensation products of a first reactant having a long fatty acid chain and at least one free hydroxyl group and a second reactant selected from the group consisting of aromatic anhydrides and aromatic acid chlorides. The first reactant is preferably an ester of a polyol and at least one $C_{12}-C_{20}$ fatty acid. The first reactant can also be an ether of a polyol and at least one $C_{12}-C_{20}$ fatty alcohol, a $C_{12}-C_{20}$ fatty alcohol itself, or mixtures of any of these reactants. Preferred polyols include glycerol, 2-ethyl-2-(hydroxymethyl)-1,3-propanetriol, erythritol, pentaerythritol, ethylene glycol, propylene glycol, trimethylene glycol, and mixtures thereof. Preferred fatty acids are selected from the group consisting of lauric acid, myristic acid, palmitic acid, palmitoleic acid, linoleic acid, linolenic acid, oleic acid, stearic acid, isostearic acid, arachidonic acid, and mixtures thereof. Most Preferred first reactants are glycerol monostearate, glycerol distearate, glycerol monopalmitate, glycerol dipalmitate, glycerol monooleate, glycerol dioleate, and mixtures thereof.

The preferred anhydrides or acid chlorides are selected, in part, on how many free hydroxyl groups are on the first reactant. Since highly polymerized alkyds are not good vesicles formers, the first reactant and second reactant should be selected such that they do not easily polymerize. If the reactants can polymerize, the stoichiometric ratios of the reactants are selected to minimize polymerization. For example, if a glycerol monooleate is selected as a first reactant, a very reactive anhydride such as trimellitic anhydride would not be appropriate; rather, less reactive aromatic anhydrides such as phthalic anhydride would be preferred. In like manner, if glycerol distearate was used as the first reactant, a more reactive anhydride such as trimellitic or hemimellitic anhydride would be preferred. While acid chlorides may be used to practice the invention, the anhydrides are most preferred since the aromatic anhydrides are more reactive than the aromatic acid chlorides. The anhydrides and acid chlorides most preferred for the present invention are those of phthalic acid, trimellitic acid, trimeric acid, hemimellitic acid, pyromellitic acid, and mixtures thereof.

While the combination of the aromatic anhydrides and the glycerol fatty acid esters are preferred, similar fatty acid ethers or alcohols could be used as the first reactant. The preferred fatty acid chains are from lauric, myristic, palmitic, palmitoleic, ceytl, stearic, isostearic, oleic, linoleic, linolenic, or arachidonic acids.

The invention further features a method of producing lipid vesicles using these alkyds The alkyds are prepared, of necessity, in a non-aqueous solution. The alkyds are separated and made into a liquid form, e.g., by heating. The alkyds are neutralized with a base such as sodium hydroxide, until a pH above the pK value, normally about pH 6 or more. The alkyds are then be hydrated using standard hydrating procedures. One procedure which works exceptionally well is the syringe method described in U.S. Pat. No. 4,855,090, the disclosure of which is incorporated herein by reference. The neutralization step can take place before hydration or simultaneously with the hydration by using an aqueous solution of a base such as sodium hydroxide as the hydrating solution. If any aqueous soluble materials are to be encapsulated in the vesicles, they can be incorporated in the hydrating solution. Oils which do not dissolve the alkyds can also be incorporated into the vesicles, and the oils can carry dissolved or suspended oil soluble material.

The preferred vesicles of the invention are paucilamellar lipid vesicles. These paucilamellar lipid vesicles are easily obtained using the procedures described in U.S. Pat. No. 4,911,928 for hydrating a lipid phase with an aqueous phase or by using a machine such as described in U.S. Pat. No. 4,895,452. The disclosures of both of these patents are incorporated herein by reference. However, if classic methods such as the Bangham method are used, see J.Mol.Biol. pp. 238-252 (1965), multilamellar vesicles may be formed. It is also possible to use these materials to form unilamellar lipid vesicles using any standard procedure, see, e.g., the procedures described in U.S. Pat. No. 4,853,228, the disclosure of which is also incorporated herein by reference.

DETAILED DESCRIPTION OF THE INVENTION

The present invention features lipid vesicles having a monomeric or dimeric alkyd as a primary wall-forming material. Other materials such as cholesterol and other sterols may also be used in the lipid walls. The preferred vesicles of the invention are paucilamellar lipid vesicles, vesicles having about 2-10 lipid bilayers surrounding a large, unstructured amorphous center. This amorphous center may be filled with an aqueous solution or an oil which does not dissolve the alkyd. Large quantities of aqueous and/or oil soluble material may be carried in this amorphous center.

Briefly, the preferred alkyds of the invention are those which have a glycerol backbone, at least one $C_{16}$-$C_{18}$ fatty acid attached thereto through ester linkage, and a large aromatic head group such as obtained using phthalic anhydride. The reaction product is shown below

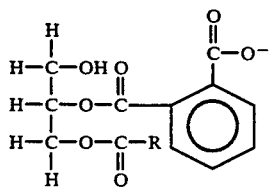

This monomer has a polar head group which includes the carboxylic acid and an apolar tail in the form the long chain (e.g., $C_{16}$-$C_{18}$) fatty acid. Other combinations of the reactants described herein will lead to similar molecules having polar head groups and apolar tails. The polar head groups are hydrated while the apolar tails are in an apolar environment.

The alkyd will not form vesicles so long as the carboxylic acid is unneutralized. Sodium hydroxide or another base is needed to neutralize the acid because until the pH of the solution is above the pK point of the acid, normally a pH of about six, vesicles cannot form. Once neutralized, however, the alkyd will form vesicles using any standard hydrating procedure.

The following Examples will more clearly illustrate the methods and products of the invention.

EXAMPLE 1

This Example shows the use of a reaction between phthalic anhydride and glycerol monostearate to form an alkyd which was made into the vesicles of the invention. A condensation reaction was carried out using 3 g of phthalic anhydride (Sigma Chemical Company) and 7.251 g of glycerol monostearate (Protameen Chemicals, Inc.). The amounts of reactants are chosen based on their formula weights to be in 1:1 stoichiometric ratios. Both of these reactants are white powders so 2 g xylene was added as a solvent. The material is placed in a Erlynmeyer flask with a reflux apparatus on top to recycle the xylene. A small amount (approximately 60 mg) HCl was added as a catalyst but further experiments showed that this acid was not necessary. The reactants were heated to 150°-180° C. for 2-4 hours. A waxy precipitate formed and was separated.

The resulting alkyd was heated to 50°-70° C. until melted. Approximately 1 ml of the alkyd was mixed with 8 ml of 0.0125 N NaOH to form a first solution and a solution of 8 ml of 0.001 N HCl was prepared as a second solution. The two solutions were each placed in syringes connected by a stopcock and syringed back and forth for approximately two minutes. The vesicles formed in less than the two minutes and upon examination, were determined to be paucilamellar lipid vesicles.

In later experiments using the same materials, 0.1 N NaOH was used as a hydrating solution without the hydrochloric acid. Using the same syringe method, acceptable paucilamellar lipid vesicles were formed.

EXAMPLE 2

In this Example, an alkyd was made from phthalic anhydride with a different ester, glycerol oleate (ATMOS 300). While this ester is purportedly a monooleate, it is actually approximately 46% glycerol monooleate and 40% glycerol dioleate.

One gram of the phthalic anhydride was mixed with 2.42 g of glycerol oleate, followed by the addition of 2 g of xylene and 60 mg of 0.1 N HCl as a catalyst. The reactants were again placed in an Erlynmeyer flask and the reaction was carried out as described in Example 1.

The resulting lipid was separated and 1 ml was hydrated with 4 ml of 0.1 N NaOH using the syringe method. Paucilamellar lipid vesicles were formed and separated from excess aqueous phase and excess solvent by centrifugation.

EXAMPLE 3

In this Example, glycerol monostearate and trimellitic anhydride were reacted to form an alkyd useful in the present invention. Approximately 3.9 g of trimellitic anhydride was mixed with 7.251 g of glycerol monostearate, then 3 g of xylene was added. The resulting mixture was placed in an Erlynmeyer flask with a reflux chamber attached and heated at 150° C. for four hours. The resulting alkyd was separated from unreacted material.

Vesicles were formed by heating the alkyd to 70° C. and mixing 0.5 ml of the alkyd with 4 ml of a 0.1 N NaOH solution using the syringe method described in Example 1. Again, paucilamellar lipid vesicles were formed and separated by centrifugation.

EXAMPLE 4

In this Example, glycerol monostearate and pyromellitic anhydride were used to form the alkyd. The reaction was carried out by mixing 4.42 g of pyromellitic anhydride with 7.251 g of glycerol monostearate, followed by the addition of 3 g of xylene. The same reaction procedure was used, with a four hour reflux at a boiling temperature of the xylene, approximately 150° C. Again, the alkyd was separated and used to prepare vesicles using the procedures described in Example 1. Vesicles were visible under a light microscope.

EXAMPLE 5

In this Example, glycerol distearate and trimellitic anhydride were used to form the alkyd. The reaction was carried out by mixing 6.25 g of the glycerol distearate with 1.921 g of trimellitic anhydride and 2 g of xylene. The reaction was refluxed using the same procedure as described in Example 2. Again, a separable alkyd was formed which could be made into vesicles using the procedures described in Example 1.

EXAMPLE 6

This Example shows why the proper selection of reactants is important. An action was carried out by mixing 1.503 g of 1-monomyristoyl-rac-glycerol with 0.958 g of trimellitic anhydride. The reactants were solublized using 1 g of xylene and refluxed at about 150° C. for one hour. The resulting alkyd was not usable in the invention because it polymerized rather than forming a monomer. This appears to be because the combination of the monomyristoyl-rac-glycerol and trimellitic anhydride is so easily polymerized that even using stoichiometric proportions, a polymer formed which could not be made into vesicles.

In contrast, a similar experiment was run using the same glycerol derivative but with phthalic rather than trimellitic anhydride In this case, a material useful in the invention was formed. More particularly, 1 g of the monomyristoyl-rac-glycerol was mixed with 0.489 g of phthalic anhydride followed by the addition of 1 g of xylene. After refluxing at 150° C. for at least two hours, the alkyd was separated from the reactants. The resulting lipid was mixed with 0.1 N NaOH using the syringe method described in Example 1. This alkyd formed excellent paucilamellar lipid vesicles.

EXAMPLE 7

In this experiment, ceytl alcohol was used rather than a fatty acid ester with the phthalic anhydride to form the alkyd. Approximately 2 g of ceytl alcohol was mixed with 1.214 g of phthalic anhydride and 2 ml of xylene was added. These reactants were again refluxed at 150° C. for two hours. The resulting lipid was separated.

Two different methods were used to form vesicles with this alkyd. In the first method, 0.5 ml of the lipid, heated to 60°-70° C., was mixed with 4 ml of 0.1 N NaOH at a similar temperature using syringes as a mixer. The resulting materials were then centrifuged at about 3500 rpm for fifteen minutes and the lipid vesicles were recovered from the top layer.

A second vesicle manufacturing method used 0.1 g of cholesterol added to 0.4 g of the lipid. The resulting material was melted at about 70° C. and mixed with 4 ml of 0.1 N NaOH. The same method was to form vesicles. The cholesterol addition appears to improve the vesicles stability, possibly through the ability of cholesterol to buffer the thermotropic phase transition.

EXAMPLE 8

In this Example, 0.5 g of the alkyd derivative obtained through the condensation of monomyristoyl-rac-glycerol and phthalic anhydride described in Example 6 was heated and combined with 0.24 g mineral oil (Drakeol 19) to form a lipid phase. This lipid phase was hydrated with 4 g of 0.1 N NaOH as an aqueous phase using the syringe procedure described in Example 1. Centrifugation at 3000 rpm for 15 minutes showed no separation of free oil. Microscopy confirmed that the mineral oil was encapsulated in lipid vesicles.

Those skilled in the art may recognize other methods and materials which may be used in the present invention. Such other materials and methods are included in the scope of the following claims.

What is claimed is:

1. A lipid vesicle having a monomeric or dimeric alkyd as its primary wall forming lipid material, said alkyd comprising a condensation product of
   (1) a first reactant selected from the group consisting of glycerol monosterate, glycerol distearate, glycerol monooleate, glycerol dioleate, 1-monomyristoyl-rac-glycerol, cetyl alcohol and mixtures thereof; and
   (2) a second reactant selected from the group consisting of phthalic anhydride, trimellitic anhydride, pyromellitic anhydride, and mixtures thereof.

2. A method of making a lipid vesicle by the steps of hydrating a lipid phase with an aqueous phase, said lipid phase comprising a monomeric or dimeric condensation product of p1 (1) a first reactant selected from the group glycerol monostearate, glycerol distearate, glycerol monooleate, glycerol dioleate, 1-monomyristoyl-rac-glycerol, cetyl alcohol and mixtures thereof; and
   (2) a second reactant selected from the group consisting of phthalic anhydride, trimellitic anhydride, pyromellitic anhydride, and mixtures thereof.

* * * * *